United States Patent [19]

Wainberg et al.

[11] Patent Number: 5,075,025

[45] Date of Patent: Dec. 24, 1991

[54] DISINFECTANT COMPOSITION

[75] Inventors: Mark A. Wainberg, Montreal; Chiu-Ming Wong, Winnipeg, both of Canada

[73] Assignee: Kam Scientific Inc., Winnipeg, Canada

[21] Appl. No.: 362,356

[22] Filed: Jun. 6, 1989

Related U.S. Application Data

[63] Continuation-in-part of Ser. No. 112,205, Oct. 22, 1987.

[51] Int. Cl.$^5$ .......................... C11D 1/00; C11D 3/50; C11D 3/43

[52] U.S. Cl. ....................... 252/95; 252/104; 252/156; 252/174.11; 252/99

[58] Field of Search ............... 252/95, 104, 99, 174.11

[56] References Cited

U.S. PATENT DOCUMENTS

| | | | |
|---|---|---|---|
| 2,694,722 | 11/1954 | Katz | 260/453 |
| 4,017,412 | 4/1977 | Bradley | 252/186 |
| 4,071,463 | 1/1978 | Steinhauer | 252/103 |
| 4,113,645 | 9/1978 | DeSimone | 252/95 |
| 4,196,140 | 4/1980 | Lynch | 423/197 |
| 4,287,080 | 9/1981 | Siklosi | 252/104 |
| 4,789,495 | 12/1988 | Cahall | 252/95 |
| 4,839,079 | 6/1989 | Wainberg et al. | 252/104 |

FOREIGN PATENT DOCUMENTS 267707  5/1988  European Pat. Off. .

OTHER PUBLICATIONS

Nakagawa et al., *Chem. Abstracts* (1976) 84(20):137622h.

Suzuki et al., *Chem. Abstracts (1977) 87(22):169574x*.

Primary Examiner—Paul Lieberman
Assistant Examiner—Kevin D. McCarthy
Attorney, Agent, or Firm—Dianne E. Reed

[57] ABSTRACT

This invention provides a novel disinfectant composition which is an aqueous solution containing hypochlorite and a tertiary aliphatic alcohol t-butanol. The alcohol acts as an odor masking agent and as a stabilizer for hypochlorite ions while itself possessing disinfecting properties. The composition is useful as a disinfectant.

9 Claims, No Drawings

DISINFECTANT COMPOSITION

CROSS-REFERENCE TO RELATED APPLICATIONS

This application is a continuation-in-part of U.S. patent application Ser. No. 112,205, filed 22 Oct. 1987.

TECHNICAL FIELD

This invention relates generally to disinfectant compositions, and more particularly concerns a novel disinfectant composition containing hypochlorite and a tertiary alcohol such as t-butanol.

BACKGROUND

It is known that chlorine-based disinfectants such as those containing hypochlorite, for example sodium hypochlorite, are useful in destroying pathogens such as bacteria. These disinfectants suffer from the disadvantage that they have an offensive odor of chlorine and potential users of such disinfectants object to the smell of chlorine and thus such disinfectants tend not to be the disinfectant of choice. In addition, a hypochlorite-based composition tends not to have a very long shelf-life because of the relative instability of aqueous hypochlorite.

We have now found, and herein lies our invention, that the combination of t-butanol and hypochlorite in a disinfectant composition: (1) reduces the offensive odor that results from the hypochlorite; (2) provides for a longer shelf-life because the t-butanol acts as a stabilizer for the hypochlorite; and (3) provides a composition of biocidal activity generally higher than that provided by prior art compositions.

According to the invention, as claimed herein, there is provided a novel aqueous solution containing hypochlorite ions wherein there is present a tertiary aliphatic alcohol such as t-butanol.

The art of which applicants are aware does not teach that incorporation of t-butanol into a hypochlorite disinfectant composition will provide added biocidal activity or stabilization. Siklosi U.S. Pat. No. 4,287,080 in fact suggests that alcohols having greater than 5 carbon atoms are more stable than a lower alcohol such as t-butanol, in the presence of hypochlorite. Other art suggests that the combination of hypochlorite and t-butanol is useful only in the context of a reaction, i.e., the reaction of the two compounds to produce alkyl hypochlorites (see, e.g., Katz U.S. Pat. No. 2,694,722).

SUMMARY OF THE INVENTION

Accordingly, it is a primary object of the present invention to provide a stabilized disinfectant composition comprising a hypochlorite salt and t-butanol.

It is a further object of the present invention to provide such a stabilized disinfectant composition which further contains surfactant and fragrance.

It is another object of the invention to provide a method of stabilizing an aqueous hypochlorite solution, comprising adding to a solution an amount of t-butanol effective as a hypochlorite stabilizing agent under conditions which substantially prevent degradation or reaction of hypochlorite ion.

It is still another object of the invention to provide a method of increasing the biocidal activity of an aqueous hypochlorite solution, comprising adding to a solution an amount of t-butanol effective as a biocidal agent under conditions which substantially prevent degradation or reaction of hypochlorite ion.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

As an example of an aqueous solution containing hypochlorite ions there may be mentioned an aqueous solution containing an alkali metal or an alkaline earth metal hypochlorite such as lithium, sodium, potassium, calcium or barium hypochlorite. The hypochlorite compound may be present in an amount of about 0.1 wt. % to about 2 wt. % of the solution, preferably about 0.5 wt. %. A preferred hypochlorite salt for use herein is sodium hypochlorite.

The tertiary aliphatic alcohol present in the novel aqueous hypochlorite solution may be a tertiary alcohol containing from 4 to 8 carbon atoms such as t-butanol, 2,3-dimethyl-2,3-butanediol or 2,4-dimethyl-2,4-pentanediol. Of these tertiary aliphatic alcohols, the preferred alcohol is t-butanol. The presence of a tertiary aliphatic alcohol is advantageous in that it acts as an odor masking agent for the hypochlorite, increases, as noted above, biocidal activity of the composition, and stabilizes hypochlorite ions.

As a further preferred feature of the invention there is provided an aqueous solution containing a compound providing hypochlorite ions, such as sodium, potassium, lithium or calcium hypochlorite, in the presence of a tertiary aliphatic alcohol, such as tertiary-butanol, 2,3-dimethyl-2,3-butanediol or 2,4-dimethyl-2,4-pentanediol, wherein for each 1 part by weight of said compound there is present from about 2 parts by weight to about 30 parts by weight of tertiary aliphatic alcohol, preferably from about 5 parts to about 15 parts by weight of tertiary aliphatic alcohol.

For example, an aqueous solution containing 1 part by weight of sodium hypochlorite may have present therein from about 2 parts by weight to about 30 parts by weight, preferably from about 5 parts to about 15 parts by weight, of tertiary-butanol, 2,3-dimethyl-2,3-butanediol or 2,4-dimethyl-2,4-pentanediol. A particularly useful aqueous solution is one containing about 1 part by weight of sodium hypochlorite and about 10 parts by weight of tertiary-butanol, 2,3-dimethyl-2,3-butanediol or 2,4-dimethyl-2,4-pentanediol.

The aqueous solution containing hypochlorite ions may optionally have present therein one or more additional ingredients.

For example, the aqueous solution may also contain a surfactant. While suitable surfactants may be either anionic, cationic, amphoteric or nonionic, they must not be such that they will react with or in any way degrade the other components of the composition. Representative of surfactants useful in conjunction with the present invention are esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides, may be employed as well.

A particularly preferred surfactant for use herein is sodium dodecyl sulfate. For each part by weight of compound providing hypochlorite ions, such as sodium hypochlorite, it is preferred that there be present from about 0.005 to about 0.1 part by weight, most preferably about 0.02 part by weight, of a surfactant such as sodium dodecyl sulfate.

The aqueous solution containing hypochlorite ions may also optionally have present therein one or more chlorine-stable fragrances. Suitable fragrances for use herein include virtually any fragrance that is stable to hypochlorite, e.g., benzaldehyde, lavender oil, lemon oil, methyl salicylate, phenylethyl alcohol, and the like. Such fragrances will generally be present in an amount such that for each part by weight of hypochlorite compound there is present from about 0.005 to about 0.2 part by weight of fragrance, most preferably about 0.02 part by weight of fragrance, most preferably a lemon fragrance.

The amount of fragrance may vary according to the strength and volume of the fragrance used. A weaker fragrance may be present to an extent of 0.2 wt. % whereas a stronger fragrance may be present to an extent of 0.02 wt. %. The synthetic organic detergent, such as sodium dodecyl sulfate, not only provides a cleaning power to the disinfectant but it also helps to dissolve or maintain the fragrance in solution. Since suitable fragrances mentioned above are usually oil-based fragrances, the synthetic organic detergent may be used to dissolve the fragrance prior to addition to the aqueous solution and thereafter it maintains the fragrance in solution. When a fragrance is present to an extent of from about 0.005 to about 0.2 wt. %, the range of detergent may generally be from about 0.005 to about 0.01 wt. %. Quantities of detergent in excess of this amount may be present to provide additional detergency to the solution.

Other optional ingredients may be present in the novel aqueous solution of the invention such as a chlorine-stable coloring agent.

In a preferred embodiment, then, the invention provides a stabilized disinfectant composition which contains:

about 0.1%-2.0 wt. % of a hypochlorite salt selected from the group consisting of sodium hypochlorite, lithium hypochlorite, potassium hypochlorite and calcium hypochlorite;

about 0.2%-60 wt. % t-butanol (i.e., 2-30 parts per part hypochlorite salt); and about 0.0005%-0.2 wt. % surfactant (i.e., 0.005-0.01 parts per part hypochlorite salt).

In a particularly preferred embodiment, t-butanol is present in an amount in the range of about 0.5%-30 wt. % (5-15 parts per part hypochlorite salt). When fragrance is included, it will in the preferred embodiment be present in an amount in the range of about 0.0005%-0.4 wt. % (i.e., 0.005-0.2 parts per part hypochlorite salt).

The novel aqueous solutions of this invention are useful in destroying pathogens including viruses, bacteria and fungi, in any number of contexts, including in hospitals, restaurants, home cleaning, and the like.

The invention is illustrated by, but not limited by, the following Examples in which the ingredients are given as percentages of parts by weight.

EXAMPLE 1

An aqueous solution is prepared containing 0.5 wt. % of sodium hypochlorite and 5 wt. % of tertiary-butanol. There is thus obtained a disinfectant solution having an acceptable masked chlorine odor compared with a corresponding 0.5 wt. % sodium hypochlorite solution containing no tertiary-butanol.

The 0.5 wt. % of sodium hypochlorite may be replaced by 0.5 wt. % of potassium, lithium or calcium hypochlorite and there is likewise obtained a satisfactory and acceptable disinfectant solution.

The 5 wt. % of tertiary-butanol may be replaced by 5 wt. % of 2,3-dimethyl-2,3-butanediol or 2,4-dimethyl-2,4-pentanediol and there is likewise obtained a satisfactory and acceptable disinfectant solution.

EXAMPLE 2

An aqueous solution is prepared containing 0.5 wt. % of sodium hypochlorite, 5 wt. % of tertiary-butanol and 0.01 wt. % of sodium dodecyl sulfate. There is thus obtained a disinfectant solution having an acceptable masked chlorine odor.

The 0.5 wt. % of sodium hypochlorite may be replaced by 0.5 wt. % of potassium, lithium or calcium hypochlorite and there is likewise obtained a satisfactory and acceptable disinfectant solution.

The 5 wt. % of tertiary-butanol may be replaced by 5 wt. % of 2,3-dimethyl-2,3-butanediol or 2,4-dimethyl-2,4-pentanediol and there is likewise obtained a satisfactory and acceptable disinfectant solution.

EXAMPLE 3

An aqueous solution is prepared containing 0.5 wt. % of sodium hypochlorite and 2.5 wt. % of tertiary-butanol, 2,3-dimethyl-2,3-butanediol or 2,4-dimethyl-2,4-pentanediol. There is thus obtained a disinfectant solution having an acceptable masked chlorine odor compared with a corresponding sodium hypochlorite solution containing no tertiary-butanol.

EXAMPLE 4

An aqueous solution is prepared containing 0.5 wt. % of sodium hypochlorite and 7.5 wt. % of tertiary-butanol, 2,3-dimethyl-2,3-butanediol or 2,4-dimethyl-2,4-pentanediol. There is thus obtained a disinfectant solution having an acceptable masked chlorine odor compared with a corresponding sodium hypochlorite solution containing no tertiary-butanol.

EXAMPLE 5

An aqueous solution is prepared containing the following ingredients:
0.5 wt. % of sodium hypochlorite;
5.0 wt. % of tertiary-butanol;
0.01 wt. % of sodium dodecyl sulfate; and
0.01 wt. % of lemon fragrance.

There is thus prepared an aqueous disinfectant solution which has an acceptable masked chlorine odor when used for its intended purpose of destroying pathogens.

The 0.5 wt. % of sodium hypochlorite may be replaced by 0.5 wt. % of potassium, lithium or calcium hypochlorite and there is likewise obtained a satisfactory and acceptable disinfectant solution.

The 5 wt. % of tertiary-butanol may be replaced by 5 wt. % of 2,3-dimethyl-2,3-butanediol or 2,4-dimethyl-2,4-pentanediol and there is likewise obtained a satisfactory and acceptable disinfectant solution.

We claim:
1. A stabilized disinfectant composition comprising, in aqueous solution:
   about 0.5-2.0 wt. % of a hypochlorite salt selected from the group consisting of sodium hypochlorite, lithium hypochlorite, potassium hypochlorite and calcium hypochlorite;
   about 1.0-60 wt. % t-butanol; and
   about 0.00025-0.2% wt. % synthetic organic detergent.

2. The composition of claim 1, wherein t-butanol is present in an amount in the range of about 2.5-30 wt. %.

3. The composition of claim 1, further including fragrance.

4. The composition of claim 3, wherein the fragrance is present in an amount in the range of about 0.00025%-0.4 wt. %.

5. The composition of claim 4, wherein the fragrance is lemon oil.

6. The composition of claim 4, wherein the fragrance is pine oil.

7. The composition of claim 1, wherein the synthetic organic detergent is sodium dodecyl sulfate.

8. A stabilized disinfectant composition comprising, in aqueous solution:
   about 0.5-2.0 wt. % of sodium hypochlorite;
   about 1.0-60 wt. % t-butanol; and
   about 0.00025-0.2% wt. % sodium dodecyl sulphate; and
   0.00025-0.2 wt. % fragrance.

9. A stabilized disinfectant composition comprising, in aqueous solution:
   about 0.5-2.0 wt. % of sodium hypochlorite;
   about 2.5-30 wt. % t-butanol; and
   about 0.00025-0.2% wt. % sodium dodecyl sulphate, and
   0.00025-0.2 wt. % fragrance.

* * * * *